United States Patent [19]

Crowder

[11] Patent Number: 4,560,875
[45] Date of Patent: Dec. 24, 1985

[54] INFRARED ABSORPTION GAS DETECTOR

[75] Inventor: John G. Crowder, Edinburgh, Scotland

[73] Assignee: EIGD Limited, Wetherby, United Kingdom

[21] Appl. No.: 596,349

[22] Filed: Apr. 3, 1984

[30] Foreign Application Priority Data

Apr. 5, 1983 [GB] United Kingdom ............... 8309211

[51] Int. Cl.$^4$ ........................... G01J 1/00; G01J 1/42
[52] U.S. Cl. .................................. 250/343; 250/339; 250/353
[58] Field of Search ............... 250/338 PY, 339, 343, 250/344, 345, 346, 372, 341, 353

[56] References Cited

U.S. PATENT DOCUMENTS

| 4,320,297 | 3/1982 | Cederstrand et al. | 250/343 |
| 4,358,679 | 11/1982 | Lipoma | 250/343 |
| 4,437,005 | 3/1984 | Ophoff et al. | 250/351 |

Primary Examiner—Alfred E. Smith
Attorney, Agent, or Firm—Sughrue, Mion, Zinn, Macpeak and Seas

[57] ABSTRACT

An infrared absorption gas detector uses the amount of IR radiation of a particular wavelength to indicate the presence of a particular component or gas. A monitoring head for such a detector includes a source (8) of IR radiation, dual IR detector elements (17, 18), an optical path which extends between the source and the elements and which includes a gas sample volume, and selectively transmitting spectral filters (20, 21) immediately in front of the detector elements (17, 18) to filter the radiation impinging on them. The optical path also includes a concave mirror (9) to provide a converging beam of radiation concentrated onto both elements of the detector. The location of the gas sample volume, the separation of the two detector elements (17, 18) of the detector, and the mirror are arranged so that IR radiation emitted by the source and impinging upon each of the detector elements follows a substantially common path through the gas sample volume. The monitoring head operates, in effect, as a single beam in both space and time while having no moving parts.

18 Claims, 5 Drawing Figures

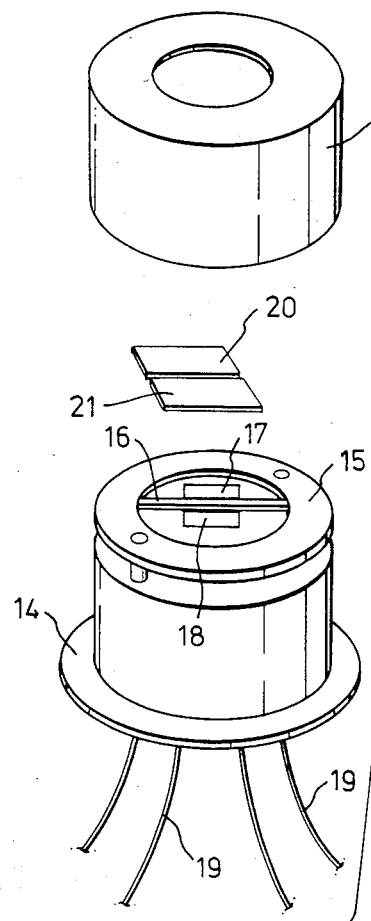
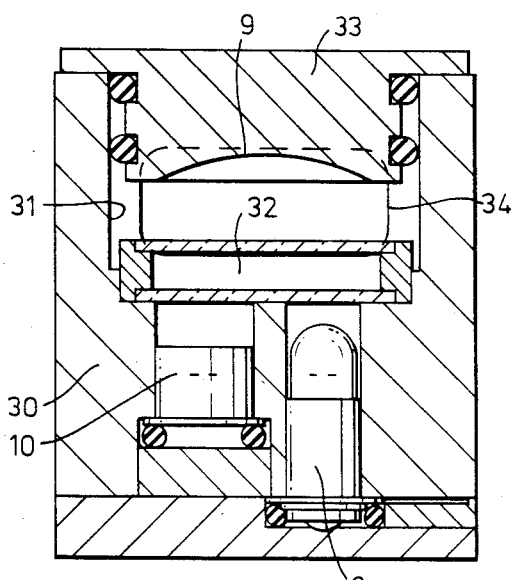
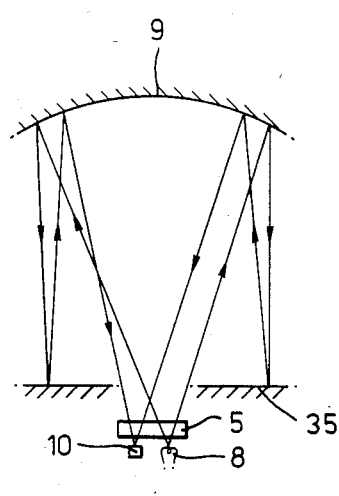
Fig. 2.
Fig. 4.
Fig. 5.

INFRARED ABSORPTION GAS DETECTOR

BACKGROUND OF THE INVENTION

This invention relates to an infrared absorption gas detector in which the amount of infrared radiation absorbed by a gas mixture gives an indication of the presence of particular components within that gas.

The present invention is particularly concerned with infrared absorption gas detectors which are used to detect the presence of a particular gas, and, for example, trigger an alarm when the concentration of that gas exceeds a predetermined value. Such gas detectors can be used to detect a wide variety of gases the presence of which represents a hazard or danger. Such gases include common non-life supporting gases like carbon dioxide, toxic gases such as carbon monoxide or hydrogen sulphide, and flammable gases such as those in the methane series, methane, ethane, propane, butane, and vapours of flammable liquids.

At present, infrared absorbing gas detectors have monitoring heads which fall into two different and separate categories. Firstly, there are infrared absorption gas detectors which have a monitoring head using a double beam in space system in which two beams of infrared radiation traverse two different and separate paths in space through an atmosphere to be monitored and these two beams are filtered along their path so that they have different wavelengths. Both beams are usually derived from the same source but then follow different paths through the atmosphere to be monitored, and the resulting intensities of the two beams are detected by two independent radiation detectors. One of the beams serves as a reference beam by which allowance can be made for variations in the radiation output of the source and for changes in the sensitivity of the radiation detectors as a result of, for example, changes in ambient temperature while the other beam is the one which is absorbed by the gas to be detected. However, since two separate radiation detectors are used, difficulties are caused when the two detectors are not perfectly matched. Even if the detectors are matched reasonably well, differences still occur as a result of the ageing properties of the two radiation detectors and hence their operating conditions may also be different, for example, their temperatures may be different. Also no allowance can be made for any change in the transmission of the optical paths extending between the source and the detectors since the two beams travel over essentially different optical paths. The transmission of the two optical paths changes in use due the accretion of dust or debris on any surface in the optical path, and since the two optical paths are substantially independent through the atmosphere to be monitored any non-uniform accretion of dust or debris causes an imbalance between the two paths.

Often such double beam in space systems also include a chopper wheel which interrupts the output of the source to provide a pulsed beam of radiation. The chopper wheel may also be used to control the radiation emitted by the source and direct it along one path or the other. This is a further disadvantage since moving parts tend to wear, leading to unreliability. They also lead to the gas detector not being as robust as possible.

An example of this type of gas detector is described in U.S. Pat. No. 4,320,297, wherein the two beams follow two separate paths through the same sample gas cell and a chopper wheel is also included in this example of detector to interrupt the beam.

Secondly, the other conventional type of infrared gas absorption detector has a monitoring head which uses a double beam in time system whereby two beams of different wavelength alternately travel over the same optical path and are detected using the same radiation detector. This type of gas detector must include some means to change the wavelength of the beam and, normally, this has the form of a filter wheel which interposes spectral filters having different pass bands into the optical path between the source and the radiation detector. The filter wheel also acts as a chopper wheel to provide a pulsed source of radiation. Naturally, such an infrared absorption gas detector does permit some allowance to be made for changes in the transmission of all of the common parts of the optical path i.e. changes in transmission of all parts except the spectral filters, and thus allowance can be made for the non-uniform accretion of dust on surfaces of the optical path. The main disadvantage with this type of gas detector is the need for the means to introduce different spectral filters in the optical path which requires the gas detector to include moving parts and this leads to wear and unreliability, and thus to the gas detector not being as robust as possible. One example of a detector of this type is described in U.S. Pat. No. 4,358,679.

U.S. Pat. No. 3,539,804 discloses a small and compact gas detector for detecting carbon dioxide. This gas detector is essentially a double beam in space system. The monitoring head of the gas detector includes a single source of radiation, two detectors for detecting infrared radiation, an optical path extending between the source and the detectors, which includes a gas sample volume, and a selectively transmitting spectral filter located in the optical path leading to at least one of the detectors. In this example the source of infrared radiation is a conventional pre-focus bulb with a tungsten filament which provides a non-pulsed, concentrated but diverging beam of infrared radiation through the gas sample volume. The two detectors receive radiation that has passed through two different, but closely spaced, regions of the gas sample volume since the output beam of the source of infrared radiation diverges slightly. The radiation which impinges on one of the detectors thus forms a reference beam and that impinging on the other the analytical beam, and the filter located in front of at least one of them modifies the wavelength of that part of the radiation to provide the difference in wavelength between the beams.

Although in this example the two detectors receive radiation from adjacent portions of the gas sample volume, there are essentially still two separate and independent beams and thus this example has all the limitations of the conventional double beam in space system and any uneven contamination of the bulb and pre-focus lens or any contamination of a downstream window of the gas detector leading to the infrared radiation detectors and filters leads to an imbalance in the system. Indeed the disclosure in U.S. Pat. No. 3,539,804 does discuss the inclusion of a neutral density filter covering half the entry window to the infrared radiation detector assembly and how, by rotating this, it is possible to cause an imbalance between the two beams to try to match the response of the two radiation detectors. However, such a method can only be used during the initial set up of the instrument and does not take any account of the changes in the contamination of the monitoring head during use. This patent also discloses that some of these problems in the system can be overcome by moving the selectively transmitting spectral filter into and out of the optical path between the source and one of the radiation detectors, and so convert this apparatus into one operating as a double beam in time system.

SUMMARY OF THE INVENTION

According to this invention a monitoring head for an infrared absorption gas detector including a source of infrared radiation, two detectors for detecting infrared radiation, an optical path which extends between the source and the detectors and which includes a gas sample volume and a selectively transmitting spectral filter to filter the radiation leading to one of the detectors, also includes as characteristic features that the two detectors are the two elements of a dual element detector, that the filter is located immediately in front of one of the dual elements of the detector, and that the optical path also includes converging means to provide a converging beam of radiation concentrated onto both elements of the dual element detector. The location of the gas sample volume, the separation of the two elements of the dual element detector, and the converging means are arranged such that infrared radiation emitted by the source and impinging upon each of the elements of the dual element detector follows a substantially common path through the gas sample volume.

The monitoring head in accordance with this invention enables the detector to operate, in effect, as a single beam in both space and time while requiring no moving parts whatsoever. By using the dual elements of a dual element radiation detector not only can the two elements of the radiation detector be located very close together, which facilitates the commonality of the path followed by the infrared radiation impinging on the two elements of the detector, but also the critical parameters of both elements are matched and substantially identical. Dual element detectors have both elements on the same substrate and formed identically by the same series of manufacturing steps. Examples of such dual element radiation detectors are dual element pyroelectric detectors and dual element thermopile detectors. Typically the two elements of such detectors are less than 2 mm apart and frequently they are only separated by 0.5 mm.

Since the dual elements of the radiation detector are so close together and since the optical path includes converging means to provide a converging beam of incident radiation which is concentrated onto both elements of the dual element detector, the radiation that impinges upon the two elements of the dual element detector has travelled over substantially identical paths through the gas sample volume. Thus any contamination of that path, for example any contamination in the form of an accretion of dust or debris on any member of the optical path, has virtually no differential effect on the radiation received by the two detectors. Naturally since the two elements of the detector are slightly spaced from one another the radiation received by them does not follow absolutely identical paths, but there is typically as much as a tenfold improvement in the susceptibility of the monitoring head of the gas detector to uneven contamination of its optical path.

Preferably one selectively transmitting spectral filter is mounted immediately in front of each of the two elements of the dual element radiation detector and, in this case, the pass band of each of the selectively transmitting spectral filters is different. The filters are arranged so that one of the spectral filters transmits a pass band which is strongly absorbed by the gas to be detected and this filter defines the analysing component of the beam, while the other of the spectral filters transmits a pass band which is not strongly absorbed by the gas to be detected, nor any other gas which is likely to be present, and this filter defines the reference component of the beam. Ideally the passbands of the two filters are also selected to be as close as possible to each other to minimise their signal level differences.

For example when the monitoring head is to be used for detecting the presence of carbon dioxide in an air mixture the spectral filter to provide the reference beam usually has a central wavelength of 3.95 microns and a bandwidth of 2% and the analysis filter has a central wavelength of 4.25 microns and again a bandwidth of 2%. However when the monitoring head is to be used for detecting the presence of carbon dioxide in an atmosphere where nitrous oxide may also be present, for example in an operating theatre, a reference filter having a central wavelength of 3.75 microns is used since radiation of wavelength 3.95 microns is strongly absorbed by nitrous oxide. Indeed when detecting nitrous oxide a filter having a central wavelength of 3.95 microns is used as the analysis filter. For detecting flammable gases in an environment such as an oil field the majority of flammable gases which are likely to be encountered include a carbon hydrogen bond which strongly absorbs infrared radiation. To detect such flammable gases an analysis filter having a 3.32 micron central wavelength and a bandwidth of 2% is used.

The source is preferably formed by a conventional tungsten filament lamp having a quartz or glass envelope. However such a source can only be used with spectral filters having a pass band with a wavelength of up to 4.5 microns. When operating outside this region it is preferred that the source comprises a tungsten filament bulb the envelope of which includes an infrared transmitting window or a bare non-oxidising filament which operates stably in air. Typically the source is driven by a time varying electrical current so that the output radiation from the source is pulsed. For example the output may be pulsed at a frequency of the order of 10 Hz. Pulsing the infrared source at this frequency typically matches the maximum frequency response characteristics of a thermopile or pyroelectric type of radiation detector and the pulsing frequency is usually matched to that of the radiation detector used. Naturally, the use of a varying intensity infrared source increases the sensitivity and stability of the device and has all the advantages of the other conventional infrared absorption gas detectors that include a mechanical chopper to interrupt the beam between the source and the radiation detector but of course has the advantage of not requiring the use of any moving parts.

The monitoring head may have a straight line configuration with the source at one end of the line and with the radiation detector at the other end of the line remote from the source. In this case the converging means to concentrate infrared radiation is a lens located between the source and the radiation detector, the lens providing the converging beam of infrared radiation concentrated onto both elements of the dual element detector. However, it is preferred that the monitoring head has a "folded" configuration and the converging means to concentrate infrared radiation comprises a concave mirror or a mirror and lens combination. In this case the beam traverses the gas sample volume twice. The monitoring head may also have a "double folded" configuration and so include a combination of mirrors such as a spherical concave mirror and an annular plane mirror so that the infrared radiation traverses the gas sample volume four times. Such a configuration is especially good for detecting gases that are only weak absorbers of infrared radiation.

When the monitoring head has a "folded" configuration the infrared source and the dual element radiation detector are preferably located side-by-side and are shielded from one another to prevent the radiation emitted from the source impinging directly on the elements of the radiation detector. In this case both the source and the radiation detector then face the mirror and when the mirror is a concave spherical mirror the radiation from the source is then reflected and concentrated on the radiation detector by the spherical concave mirror. Such an arrangement is particularly preferred because it not only reduces the overall length of the apparatus because of the double pass of the infrared radiation through the gas sample volume but also enables the source and radiation detector, to both of which electrical connections have to be made, to be located close together. The mirror, which is completely passive, is remote from the source and radiation detector. Typically the mirror is spaced between 10 and 100 mm away from both the source and radiation detector.

In a monitoring head including a spherical concave mirror wherein the separation of the two elements of the radiation detector is S; the distance from the two elements of the radiation detector to their entrance window is h; the separation of the mirror wherein and the entrance window is G and the diameter of the mirror is M, the degree of overlap $O_v$ at the entrance window to the radiation detector of the radiation that impinges on both elements of the detector is given by the following equation:

$$O_v = 1 - \frac{4SG}{hm\pi + 2SG}$$

Such degree of overlap may be envisioned by considering that the infrared radiation relected from the mirror and impinging on the two closely spaced but separate detector elements defines two cones having a common base (the mirror) but slightly spaced apices. These cones in turn define two partially overlapping circles on the surface of the entrance window, with the common or overlapping area being generally elliptical in shape. The degree of such overlap obviously increases as the window approaches the mirror (where there is total or 100% overlap) and vice versa, and represents the ratio of the elliptical common area to that of either one of the two full circles.

The entrance window of the radiation detector is the surface within the gas sampling volume located closest to the radiation detector and this is the surface the uneven contamination of which has the greatest effect on the radiation received by each element of the dual element detector. Substituting typical values for the worst practical case of a monitoring head with a short optical path length where h=9 mm; M=10 mm; G=11 mm; and S=0.5 mm, the degree of overlap at the entrance window to the detectors is greater than 90%. More usually the mirror is 50 mm away from the entrance window and thus G=50 mm. In this case it is clear that even with a separation of the detector elements S of as much as 2.5 mm the degree of overlap is still sufficiently high to give satisfactory results.

In practice the gas sample volume that is traversed by the radiation received by both elements is very much higher than the overlap between the radiation at the entrance window. A degree of overlap of as low as 50% at the entrance window means that there is over 80% overlap between the beams throughout the entire gas sample volume.

Preferably means are provided to prevent cross talk between the two elements of the radiation detector. These means may be formed by an opaque region placed between the two spectral filters and aligned with a gap between the two elements or it may simply be an opaque region covering the top or bottom of the joint between the two spectral filters. However, it is preferred that the means to prevent cross talk is formed by a physical, opaque barrier extending between the two elements of the detector. In this case the spectral filters may be mounted on the central barrier separating the two detector elements.

Preferably the monitoring head is arranged so that its optical alignment is not critical to facilitate both initial assembly and maintenance operations such as the replacement of the source. This is achieved by ensuring that the image intensity in the plane of the radiation detector is substantially uniform. This is preferably implemented by not focussing the lens or concave mirror exactly on the radiation detectors so that the radiation from the source, while concentrated, is not sharply focussed by the lens or mirror. Alternatively, or additionally, the radiation from the source may be diffused by placing a diffusing filter in front of the source or by placing the source in an integrating enclosure such as by placing the source in the optical centre of a reflecting spherical surface or at the base of a reflecting cylinder.

The gas sample volume may simple be exposed to the atmosphere to be monitored or, alternatively, the atmosphere to be monitored may be passed through the gas sample volume by, for example, a pump.

It is preferred that the monitoring head forms part of a complete infrared absorption gas detector and, in this case, the source and radiation detector are preferably located in a housing together with the remaining components of the gas detector with the source and radiation detector communicating with one another via an infrared transmitting window of the housing. In this way all of the active components and the electronics associated with the detector and source are isolated from corrosive and other harmful gases and from flammable environments. Especially when the gas detector is arranged to monitor the presence of flammable gases it is preferred that the housing is constructed sufficiently robustly to comply with flame and explosion proof safety standards.

BRIEF DESCRIPTION OF THE DRAWINGS

Various examples of monitoring heads and infrared absorption gas detectors in accordance with this invention will now be described with reference to the accompanying drawings, in which:

FIG. 2 is an exploded perspective view of a dual element thermoelectric detector;

FIG. 4 is a partly sectioned side elevation of the third example; and,

FIG. 5 is an optical diagram of a fourth example.

DETAILED DESCRIPTION OF THE DRAWINGS

Figure 1:
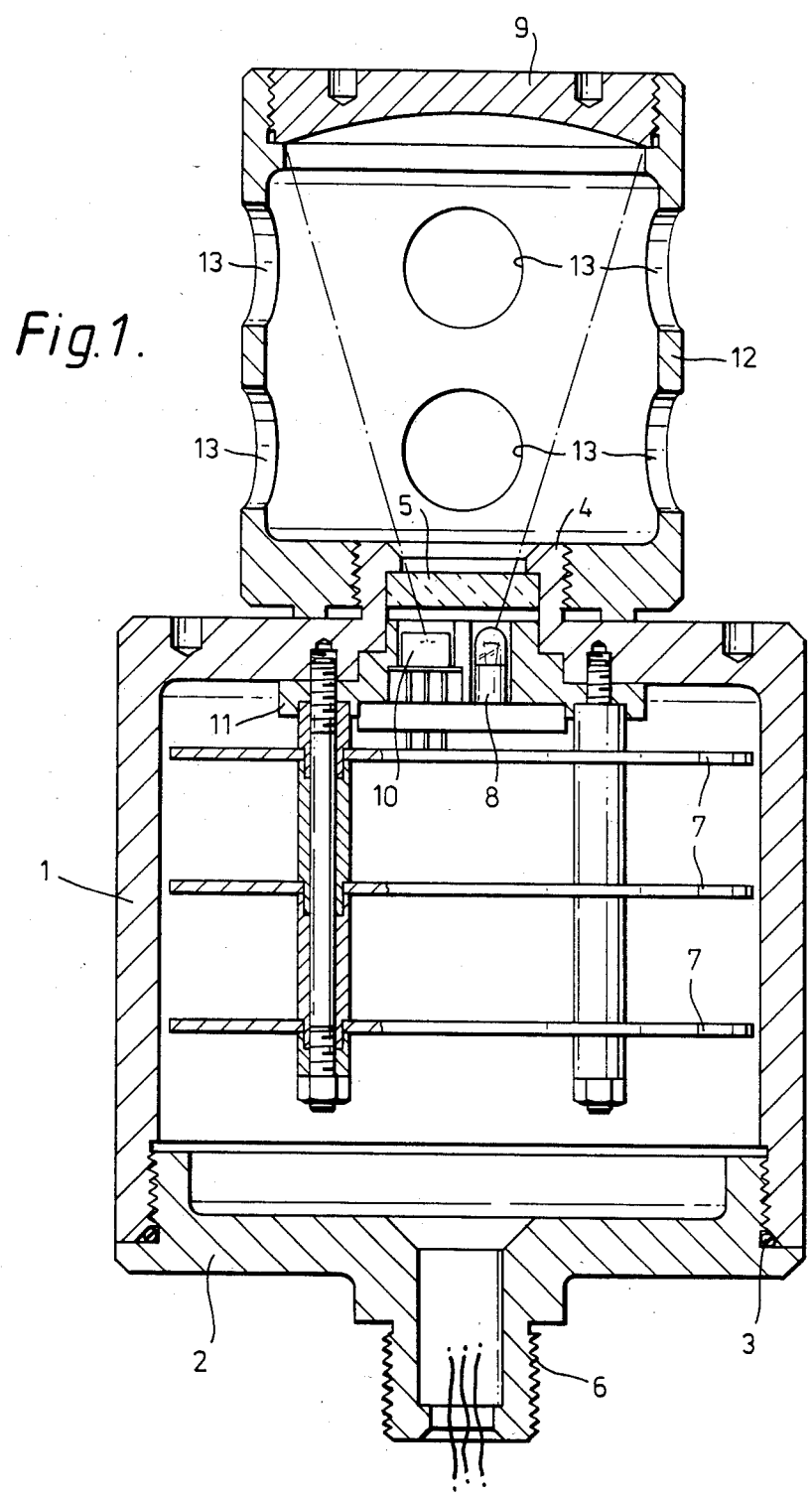
FIG. 1 is a partly sectioned elevation of the first example of a detector.

The first example of the gas detector is particularly designed to be used for the detection of flammable gases in a potentially flammable atmosphere. To meet the requirements for these conditions the electrical and electronic components of the gas detector are housed within a housing 1 having a screw threaded cover 2 and a gas-tight seal 3. The housing 1 includes a screw threaded projection 4 having an aperture in its end closed by a quartz or sapphire window 5. A screw threaded outlet 6 from the cover 2 is fixed to a standard tapped hole in a standard junction box and electrical and electronic components of the gas detector and mounted on circuit boards 7 located within the housing 1.

The monitoring head of the gas detector comprises a tungsten filament bulb 8 which forms a source of infrared radiation, a spherical concave mirror 9 and a combined detector and filter assembly 10 which will be described in more detail with reference to FIG. 2. The bulb 8 and the combined detector and filter assembly 10 are held in two side-by-side holes in a mounting block 11 housed in the housing 1. The filament of the bulb 8 and the detectors of the detector and filter assembly 10 are mounted in approximately the same plane and located beneath the window 5. A hollow cage 12 is screwed onto the outside of the screw threaded projection 4. The mirror 9 is screwed into the end of the cage 12 remote from the projection 4 and the cage 12 includes a number of apertures 13 to allow the atmosphere to be monitored to percolate freely between the window 5 and the mirror 9. In this example the gas sample volume extends between the face of the mirror 9 and the outer face of the window 5. The outer face of the window 5 defines the entrance window for radiation reaching the detectors and any contamination of the outer face of this window is likely to have the greatest differential effect on the radiation reaching the detectors. The plane containing the detector elements and the filament of the bulb 8 is located substantially at the centre of curvature of the mirror 9 and thus a diverging beam of radiation leaving the filament of the bulb 8 is concentrated by the mirror 9 onto the two elements of the detector.

FIG. 2 shows an exploded view of the detector and filter assembly 10. The detector as used in this example is a dual element, multijunction thermopile detector, model No. DR26 manufactured by the Dexter Research Center of Michigan, United States of America. The detector assembly 10 comprises a T05 style can 14 holding an annular ceramic disc 15 having a central bar 16 extending across a diameter. Two identical multijunction thermopile detector elements 17 and 18 are formed on the surface of a plastics disc, not shown, which is mounted on the base of the ceramic disc 15. The two thermopile detector elements 17 and 18 are located on opposite sides of the bar 16. Leads 19 connected to the detector elements 17 and 18 extend rearwards from the rear of the can 14. Selective spectral transmission filters 20 and 21 are mounted on top of the ceramic disc 15 and fixed in position by adhesive. The transmission filter 20 forms the analysis filter and has a centre wavelength of 3.32 microns and 2% bandwidth and the transmission filter 21 forms the reference filter and has a centre wavelength of 3.89 microns and again a 2% bandwidth. An annular cap 22 fits over the end of the can 14.

In this example the separation S of the two elements 17 and 18 is 1.1 mm; the separation h of the elements 17 and 18 from the outside surface of the window 5 is 11 mm; the separation G between the mirror 9 and the outside surface of the window 5 is 75 mm; and, the diameter of the mirror, M, is 30 mm. This means that the degree of overlap between the radiation impinging on the detector element 17 and that impinging on the detector element 18 at the outside surface of the window 5 is 73%.

Figure 3:
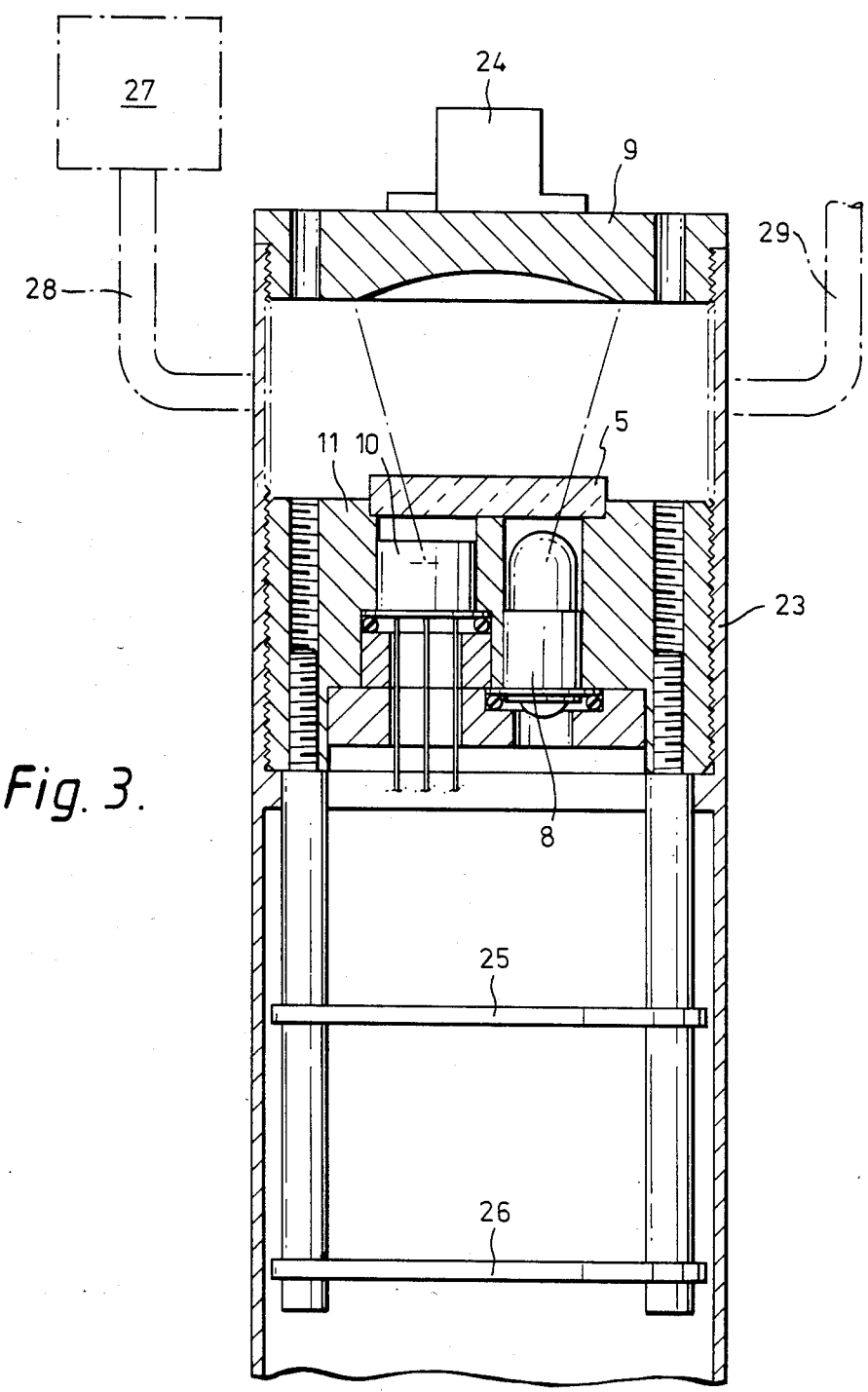
FIG. 3 is a partly sectioned and partly diagrammatic side elevation of a second example of a detector.

The second example of the gas detector in accordance with this invention shown in FIG. 3 is intended to be used in a diving bell as a sensitive detector for detecting the presence of carbon dioxide. This example is designed to trigger an alarm in the presence of 1% of carbon dioxide in the atmosphere being monitored. The second example is housed in a cylindrical casing 23 and includes a monitoring head generally similar to that used in the first example and, in general the same reference numbers are used. The monitoring head includes a cylindrical mounting block 11 containing a detector and filter assembly 10 and a tungsten filament bulb 8 housed in two adjacent bores. An infrared transparent window 5 made from sapphire or quartz is cemented to the front of the mounting block 11 to define the entrance window for the detectors and filter assembly 10. The monitoring head also includes a concave spherical mirror 9 which is mounted at the end of the casing facing the mounting block 11. This example is particularly intended for use in diving bells and other marine applications where there is considerable humidity. To prevent the mirror misting up and interferring with the response of the detectors a heater 24 is located on the rear face of the mirror 9. The cylindrical casing 23 also contains the electronics and associated electrical components of the detector. The electronic components are mounted on circuit boards 25 and 26.

The gas sample volume is defined between the outer face of the window 5 and the mirror 9. This gas sample volume may simply be open to the atmosphere to be monitored but it is preferred that the atmosphere to be monitored is positively introduced into this gas sample volume. The gas to be monitored is introduced by a pump 27 and piping 28 and 29, all of which are shown in dotted lines of FIG. 3. To protect the electronics and the electrical circuitry from the dampness it is preferred that the inside of the casing 23 behind the mounting block 11 is filled with a potting compound. The detector and filter assembly 10 is similar to that shown in FIG. 2, but as this second example is intended to detect the presence of carbon dioxide the centre wavelength of the analysis filter 20 is 4.26 microns and again has a 2% bandwidth. The reference filter 21 is the same as that used in the first example.

The dimensions in this example are as follows: S, the separation of the two detector elements is 1.1 mm; h, the separation of the radiation detector elements from the entrance window 5 is 7.5 mm; G, the separation of the mirror and the entrance window is 18.5 mm; and, M, the diameter of the mirror 9 is 11.5 mm. This gives an overlap at the outer surface of the window 5 of 75%.

The third example shown in FIG. 4 is intended for the detection of carbon dioxide in industry, typically in the cellars of public houses and other places in which cylinders containing carbon dioxide are stored. This detector is designed not to be so sensitive as that described in the second example and to give an alarm output in response to the presence of 50% of carbon dioxide in the atmosphere to be monitored. This example requires a gas sample volume with only a short absorbing path since carbon dioxide is a strongly absorbing gas. FIG. 4 shows the monitoring head of the third example which includes a cylindrical mounting block 30 in which, in adjacent bores are mounted the detector and filter assembly 10 a tungsten filament bulb 8. The block 30 includes a counter bore 31 in which is located a sealed air-filled cell 32 mounted immediately in front of the bulb 8 and detector and filter assembly 10. The monitoring head also includes a concave spherical mirror 9 formed on one face of an end plug 33 which fits into the counter bore 31. A pair of large apertures 34 are formed in the side wall of the block 30 in the counter bore 31. The gas sample volume is defined between the face of the air-filled cell 32 remote from the bulb 8 and the detector and filter assembly 10, and the mirror 9. The atmosphere to be monitored may simply percolate freely into this space by entering the apertures 34 but preferably the mounting head is mounted inside a divided housing (not shown) which includes a small fan (not shown) which draws the atmosphere to be monitored from one part of the housing to the other through the apertures 34 and hence through the gas sample volume.

The sealed air-filled cell 32 is provided in this example to increase the separation of the source 8 and detector and filter assembly 10 from the mirror 9 while, at the same time, not having too great a path length of the atmosphere to be detected to reduce the sensitivity of the device to the required limits. By locating this cell 32 adjacent the source 8 and detector 10 the overlap between the radiation reaching the analysis detector element and that reaching the reference detector element at the entrance window is increased. Such an air-filled cell 32 may be used to increase the overlap at the entrance window in the other examples. Naturally the windows of the cell 32 are formed from infrared transparent material such as quartz.

The detector and filter assembly 10 is similar to that shown in FIG. 2 and may be identical to that described with reference to the second example. Alternatively, the detector assembly may be based on a dual element pyroelectric detector such as those manufactured and distributed by Plessey Optoelectronics and Microwave Ltd. of Wood Burcote Way, Towcester, Northants, United Kingdom. Similar pyroelectric detectors may be used in the other examples.

The dimensions of the components in the third example are as follows: S, the separation of the two elements in the detector is 1.1 mm; h, the separation of the radiation detector elements from the outside of the cell 32 is 11 mm; G, the separation of the mirror 9 from the entrance window of the sample cell 32 is 7 mm; and, M, the diameter of the mirror G is 9 mm. This gives an overlap of 91%.

While in the third example in accordance with this invention it was desired to reduce the infrared path length through the gas sample volume, it is sometimes necessary to extend the path length where the gas to be detected is only a weak absorber of infrared radiation. Naturally this can be achieved by moving the mirror away from the source and detector to increase the overall length of the instrument. However, since gas detectors often have to be located in places where only a restricted space is available it is sometimes desirable to increase the path length optically by an arrangement shown in FIG. 5. In this arrangement the mounting of the source 8 and detector and filter assembly 10 are substantially the same as each of the other three examples already described, however, instead of being located at substantially the radius of curvature of the mirror 9 they are located at substantially half the radius of curvature of the mirror 9. The optical path then includes an additional, annular plane mirror 35 located adjacent the source 8 and detector and filter assembly 10. Infrared radiation emitted by the source 8 first impinges on the mirror 9 where it is reflected to the annular mirror 35. The radiation is returned from the annular mirror 35 onto the mirror 9 and, from there is reflected onto the detector and filter assembly 10. Thus, the infrared radiation makes four passes through to the gas sample volume and this doubles the sensitivity of dimensions.

I claim:

1. In a monitoring head for an infrared absorption gas detector including a source (8) of infrared radiation, two detectors (17, 18) for detecting infrared radiation, a gas sample volume, an optical path extending between said source and said detectors and passing through said gas sample volume, and a selectively transmitting spectral filter (20, 21) located in said optical path leading to at least one of said detectors, the improvement wherein said two detectors are two elements of a dual element detector and both of said elements are identically formed, closely proximate each other, on a common substrate, wherein said filter is located immediately in front of one of said dual elements of said detector, and wherein said optical path includes converging means (9) to provide overlapping and converging beams of radiation individually concentrated on said both elements of said dual element detector; the location of said gas sample volume, the separation of said two elements of said dual element detector, and said converging means being arranged such that infrared radiation emitted by said source and impinging on each of said elements of said dual element detector follows a substantially common path through said gas sample volume.

2. The monitoring head of claim 1, wherein one selectively transmitting spectral filter is located in front of each of said elements of said radiation detector, the pass band of said selectively transmitting spectral filters being different.

3. The monitoring head of claim 2, wherein said dual element radiation detector is selected from a group consisting of a dual element pyroelectric detector, and a dual element thermopile detector.

4. The monitoring head of claim 2, wherein said dual elements of said detector are spaced less than 2 mm apart.

5. The monitoring head of claim 2, wherein said beams of radiation impinging on said two elements of said radiation detector have at least 50% of their area in common when they pass through an entrance window (5) defining a downstream end of said gas sample volume.

6. The monitoring head of claim 4, wherein said beams of radiation impinging on said two elements of said radiation detector have at least 50% of their area in common when they pass through an entrance window (5) defining a downstream end of said gas sample volume.

7. The monitoring head of claim 2, wherein said converging means includes a spherical concave mirror.

8. The monitoring head of claim 7, wherein said infrared source and said radiation detector are located side by side in a common plane and are shielded from one another to prevent said radiation emitted by said source impinging directly on said detector.

9. The monitoring head of claim 6, wherein said converging means includes a spherical concave mirror.

10. The monitoring head of claim 9, wherein said infrared source and said radiation detector are located side-by-side in a common plane and are shielded from one another to prevent radiation emitted by said source impinging directly on said detector.

11. The monitoring head of claim 2, which also includes means to prevent cross talk between said two elements of said radiation detector.

12. The monitoring head according to claim 2, which also includes pump means (27-29) to draw an atmosphere to be monitored through said gas sample volume.

13. The monitoring head of claim 6, which also includes pump means (27-29) to draw an atmosphere to be monitored through said gas sample volume.

14. A monitoring head for an infrared absorption gas detector comprising a source (8) of infrared radiation; a dual element radiation detector for detecting infrared radiation, both elements of said detector being identically formed, closely proximate each other, on a common substrate; a gas sample volume; two selectively transmitting spectral filters (20, 21) individually located in front of said elements (17, 18) of said radiation detector, the pass band of said two selectively transmitting spectral filters being different, said infrared source and said radiation detector being located side-by-side in a common plane and shielded from one another to prevent radiation emitted by said source impinging directly on said detector; converging means including a mirror (9) to provide overlapping and converging beams of radiation individually concentrated on said both elements of said dual element detector; an optical path extending between said source and said dual element detector and passing through said gas sample volume; the separation of said two elements of said dual element detector, said converging means and said gas sample volume being arranged such that beams of radiation impinging on said two elements of said radiation detector have at least 50% of their area in common when they pass through an entrance window (5) defining a downstream end of said gas sample volume, whereby said beams follow a substantially common path through said gas sample volume.

15. The monitoring head of claim 14 wherein said dual element radiation detector is selected from a group consisting of a dual element pyroelectric detector and a dual element thermopile detector.

16. The monitoring head of claim 14, which also includes pump means (27-19) to draw an atmosphere to be monitored through said gas sample volume.

17. A gas detector including a monitoring head in accordance with claim 8, wherein electrical and electronic elements of said gas detector are housed with said source and said dual element radiation detector in a common, completely sealed housing, and said housing including an infrared transparent window to enable infrared radiation emitted by said source to leave said housing and pass through said gas sample volume and return to said detetor located in said housing.

18. A gas detector including a monitoring head in accordance with claim 14, wherein electrical and electronic elements of said gas detector are housed with said source and said dual element radiation detector in a common, completely sealed housing, and said housing including an infrared transparent window to enable infrared radiation emitted by said source to leave said housing and to pass through said gas sample volume and return to said detector located in said housing.

* * * * *